(12) United States Patent
Kitanaka et al.

(10) Patent No.: US 7,009,061 B2
(45) Date of Patent: Mar. 7, 2006

(54) DITERPENE COMPOUNDS

(75) Inventors: Susumu Kitanaka, Tokyo (JP); Syohei Miyata, Tokyo (JP); Liyan Wang, Shenyang (CN); Naili Wang, ShenZen (CN); Xinsheng Yao, ShenZen (CN)

(73) Assignee: Nihon University, Tokyo (JP)

( * ) Notice: Subject to any disclaimer, the term of this patent is extended or adjusted under 35 U.S.C. 154(b) by 30 days.

(21) Appl. No.: 10/767,436

(22) Filed: Jan. 30, 2004

(65) Prior Publication Data
US 2005/0043549 A1 Feb. 24, 2005

(30) Foreign Application Priority Data
Jul. 24, 2003 (JP) ............................. 2003-201340

(51) Int. Cl.
*C07D 313/00* (2006.01)
(52) U.S. Cl. ..................................................... 549/354
(58) Field of Classification Search ................ 549/433, 549/477, 354
See application file for complete search history.

(56) References Cited

OTHER PUBLICATIONS

Zheng et al., Planta medica, (1998), vol. 64, No. 8, pp. 754-756.*
S. Morris Kupchan, et al., Science, vol. 191, pp. 571-572, "Antileukemic Principles Isolated from Euphorbiaceae Plants", Feb. 1976.
Tian-Shung Wu et al., Journal of National Products, vol. 54, No. 3 pp. 823-829, "Antitumor Agents, 119'. Kansuiphorins A and B, Two Novel Antileukemic Diterpene Esters from *Euphoria Kansui*", May-Jun. 1991.
Magdalena Blanco-Molina, et al., Chemistry & Biology 8/8, pp. 767-778, "Ingenol Esters Iduce Apoptosis in Jurkat Cells Through an AP-1 and NF-kB Independent Pathway", 2001.
Li-Yan Wang, et al., "A Study for Biologically Active Compounds Extracted from *Euphorbia kansui* L. (3)", (http://202.209.162.53/123/i/multifinder.asp.), Feb. 1, 2003.
Li-Yan Wang, et al., Journal of Natural Products, vol. 65, No. 9, pp. 1246-1251, "Diterpenes from the Roots of *Euphoria Kansui* and Their in vitro Effects on the Cell Division of *Xenopus*", 2002.
Li-Yan Wang, et al., Chem. Pharm. Bull. 51(8), pp. 935-941, Diterpenes fromt the Roots of *Euphorbia kansui* and their in vitro Effects on the Cell Division of *Xenorpus* ($2^{)1,2)}$, 2003.
Hisashi Matsuda, et al., Bioorganic & Medicinal Chemistry 11, pp. 1995-2000, "Structural Requirements of Flavonoids for Nitric Oxide Production Inhibitory Activity and Mechanism of Action", 2003.

Hui-Yi Lin, et al., Biochemical Pharmacology 66, pp. 1821-1832, "Inhibition of Lipopolysaccharide-Induced Nitric Oxide Production by Flavonoids in Raw264.7 Macrophages Involves Heme Oxygenase-1", 2003.
Judit Hohmann, et al., Journal of National Products, vol. 60, No. 4, pp. 331-335, "Macrocyclic Diterpene Polyesters of the Jatrophane Type from *Euphorbia esula*", 1997.
Peter Lorenz, et al., Nitric Oxide 9, pp. 64-76, "Oxyresveratrol and Resveratrol are Potent Antioxidants and Free Radical Scavengers: Effects on Nitrosative and Oxidative Stress Derived from Microglial Cells", 2003.
Giuseppina Autore, et al., Life Sciences 70, pp. 523-534, "Inhibition Ofnitric Oxide Synthase Expression by a Methanolic Extract of *Crescentia alata* and its Derived Flavonols", 2001.
Hee Kee Kim, et al., Biochemical Pharmacology, vol. 58, pp. 759-765, "Effects of Naturally Occurring Flavonoids on Nitric Oxide Production in the Macrophage Cell Line Raw 264.7 and Their Structure-Activity Relationships", 1999.
Bernadet P. Da Silva, et al., Phytochemistry 53, pp. 87-92, "Flavonol Glycosides from *Costus spicatus*", 2000.

* cited by examiner

*Primary Examiner*—Taofiq Solola
(74) *Attorney, Agent, or Firm*—Oblon, Spivak, McClelland, Maier & Neustadt, P.C.

(57) ABSTRACT

The present invention provides a novel diterpene compounds with antineoplastic activities.

The novel diterpene compounds of the present invention are represented by the general formula (I). R1 to R6 in the formula represent an aliphatic group, or a radical represented by the general formula RCO—, wherein R represents an aliphatic, an aromatic or a heteroaromatic group. The compounds of the present invention may be prepared by extracting roots of Euphorbia kansui L. with an organic solvent such as chloroform, ethyl acetate and butanol. These extracted compounds may be used as starting materials for the preparation of the compounds represented by the general formula (I). The compounds of the present invention have antineoplastic activities, and therefore, useful as antineoplastic agents.

(I)

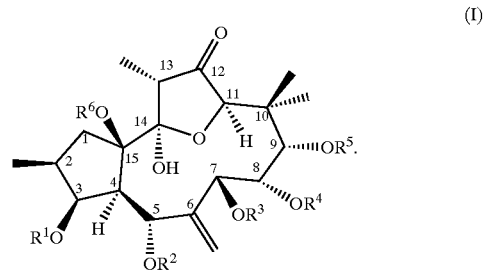

3 Claims, No Drawings

DITERPENE COMPOUNDS

TECHNICAL FIELD OF THE INVENTION

The present invention relates to novel diterpene compounds isolated from Kan Sui, which is useful as antineoplastics.

PRIOR ART

Kan Sui (Euphorbia kansui L.) is a perennial plant belonging to Euphorbiaceae and growing in northwest China. Kan Sui has been used in China as herbal remedy for treating allergic diseases such as chronic bronchitis and bronchial asthma, and malignant tumors such as esophagus cancer and breast cancer. Investigations of components in Kan Sui began in about 1943 and over ten diterpene and triterpene compounds have been found to date. Recent studies have shown that some of these diterpene compounds have anti-cancer activity, antiviral activity and cytotoxic activity, and thus, many investigators pay attention to these compounds.

S. M. Kupchan et. al. showed that Ingenol derivatives extracted from Euphorbia esula L. and represented by the general formula (1) below have depressive activities against P-388 lymphocytic leukemia in mice. (S. Morris Kupchan, et. al., Science, Vol. 191, pp. 571–572, 13, Feb., 1976.)

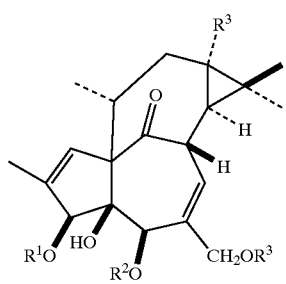

(1)

Tian-Shung Wu et. al. showed that kansuiphorin A and kanusiphorin B extracted from the roots of Euphorbia kansui L. and represented by the general formulae (2) and (3) respectively, have depressive activities against P-388 cells in vivo. (Tian-Shung Wu, et. al., J. Nat. Prod., Vol. 54, No. 3, pp. 823–829, 1991.)

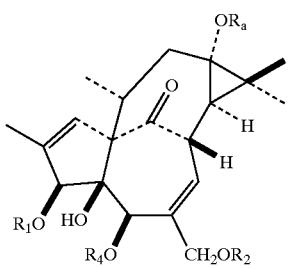

(2)

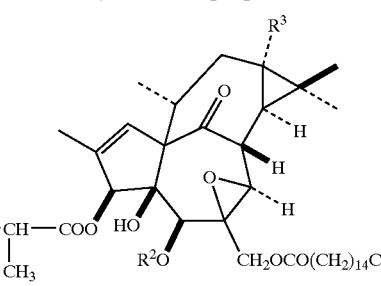

(3)

Magdalena Blanco-Molina et. al. stated that Ingenol derivatives represented by the general formula (4) below were possible to induce apoptosis in Jurkat cells. (Magdalena Blanco-Molina, et. al., Chemistry & Biology, 8/8, pp. 767–778, 2001.)

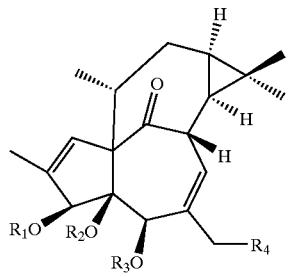

(4)

However, any prior art does not disclose compounds of the present invention.

(Problem to be Solved)

An object of the present invention is to provide novel diterpene compounds with antineoplastic activities.

(Means for Solving the Problem)

Novel diterpene compounds of the present invention are represented by the following general formula (I).

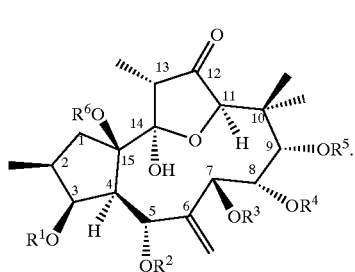

(I)

in which, $R^1$, $R^2$, $R^3$, $R^4$, $R^5$ and $R^6$ may be same or different and represent hydrogen atoms, liner or branched, saturated or unsaturated, substituted or unsubstituted aliphatic groups, or radicals represented by the general formula RCO—, wherein R denotes a liner or branched, saturated or unsaturated, substituted or unsubstituted aliphatic group, a substituted or unsubstituted aromatic or heteroaromatic group.

The compounds represented by the formula (I) are useful as a therapeutic agent for treating malignant tumors, such as esophagus cancer, breast cancer, and so on.

(Mode for Carrying Out the Invention)

$R^1$, $R^2$, $R^3$, $R^4$, $R^5$ and $R^6$ in the formula (I) represent preferably liner or branched, saturated or unsaturated aliphatic groups containing preferably from 1 to 30 carbon atoms, and more preferably from 1 to 16 carbon atoms. The aliphatic group may be substituted with a halogen atom, a hydroxyl group, an ether group, a carbonyl group, a carboxyl group, an amino group and an amide group.

Examples of carboxylic acids from which the RCO— radical wherein R represents an alkyl radical is derived include saturated aliphatic acids containing from 1 to 16 carbon atoms, such as acetic acid, propionic acid, butyric acid, 2,3—dimethyl butanoic acid, caprylic acid, capric acid, lauric acid, myristic acid, palmitic acid, and unsaturated aliphatic acids containing from 3 to 16 carbon atoms, such as 2,4—decadienoic acid. Examples of carboxylic acids from which the RCO— radical wherein R represents an aromatic radical is derived include aromatic carboxylic acids, such as benzoic acid, phthalic acid, salicylic acid, and anthranilic acid. Examples of caboxylic acid from which the RCO— radical wherein R represents an heteroaromatic radical is derived include furancarboxylic acid, thiophenecarboxylic acid, pyridinecarboxylic acid, such as nicotinic acid and iso-nicotinic acid. The aromatic and heteroaromatic radicals may be substituted with halogen atoms, hydroxyl radicals, ether radicals, carbonyl radicals, carboxyl radicals, amino radicals, and amide radicals.

A compound represented by the general formula (I), wherein $R^1$ to $R^3$, $R^5$ and $R^6$ are acetyl radicals and $R^4$ is a benzoyl radical (Compound 5) and a compound represented by the general formula (I), wherein $R^1$ to $R^3$ and $R^6$ are acetyl radicals, $R^4$ is a benzoyl radical and $R^5$ is a nicotinoyl radical (Compound 8) are prepared by extracting raw or dried, and preferably ground roots of Euphorbia kansui L. with organic solvents, such as chloroform, ethyl acetate and butanol at a room temperature, and then purifying the extracts according to known procedures.

These extracted compounds may be used as starting materials for the preparation of other compounds represented by the general formula (I). For example, Compound 5 is hydrolyzed to give the compound of formula (I) wherein $R^1$ is a hydrogen atom, and then the obtained hydroxyl compound is converted to ether compounds of the present invention in accordance with the Williamson Synthesis described below, that is, by the action of sodium alkoxides and then alkyl halides R'X wherein R' has the same meaning as $R^1$ and X represents a halogen atom:

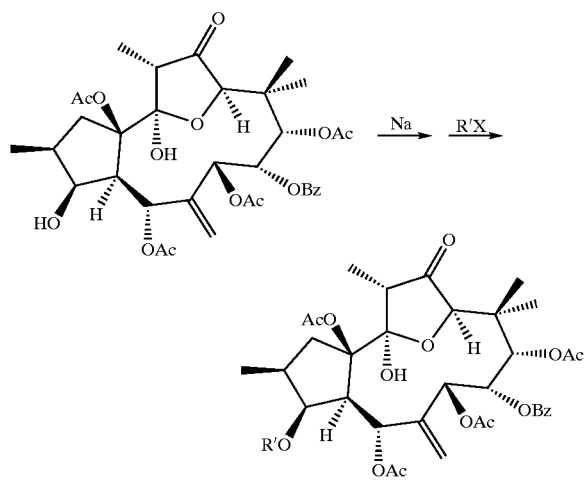

Further, the hydrolyzed Compound 5 wherein $R^1$ is a hydrogen atom may be reacted with acid anhydrides, i.e., $(R''CO)_2O$ as described below in the presence of anhydrous pyridine to give ester compounds of the present invention.

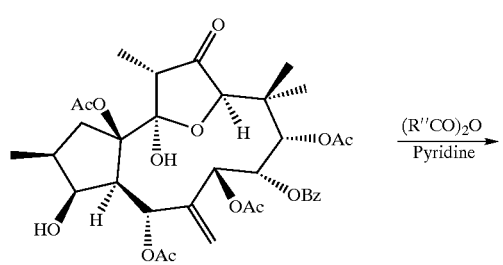

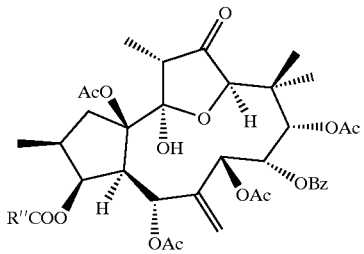

EXAMPLE 1

To 15 Kg of the dried roots of Euphorbia kansui L. collected in People's Republic of China were ground and extracted with 45 L of 60% aqueous ethanol (v/v) for 12 hours at a room temperature with stirring. The extraction was repeated again under the same conditions. The extracts were combined together and concentrated under reduced pressure at 40° C. to give a concentrated extract (1200 g). The extract was dissolved in 4 L of water and extracted with chloroform (3×4 L), ethyl acetate (3×4 L) and n-butanol (3×4 L) in this order. These fractions were concentrated under reduced pressure to give 165 g, 23 g and 64 g of concentrated extracts from the chloroform, ethyl acetate and n-butanol fractions, respectively.

150 g of the extract obtained from the chloroform fraction was subjected to silica gel chromatography (Wako gel C-300, Wako Pure Chemical Industry, 13×22 cm) and eluted with hexane/ethyl acetate gradually changed from whose ethyl acetate concentration is 0%, 2%, 3%, 5%, 10%, 20%, 30%, 50%, to 100% to give fraction Nos. 1 to 9.

EXAMPLE 2

The fraction No. 6 obtained in Example 1 (a fraction eluted with a hexane solution containing 20% of ethyl acetate) was applied to reversed phase column chromatography (ODS-7515-12A, SSC) and eluted with water/methanol gradually changed from whose water concentration is 70%, 50%, 40%, 30%, 10%, to 0% to give fraction Nos. 1 to 6.

The fraction No. 4 (a fraction eluted with a methanol solution containing 30% water) was purified by normal phase HPLC. Silica gel (Shenshu PEGASIL SILICA-60-5, 250×10 mm) was used as a stationary phase and chloroform: hexane:ethyl acetate=20:65:15 (v/v/v) was used as a mobile phase. The fraction was eluted at a flow rate of 4 ml/min (room temperature) and eluents were monitored by a UV detector at 254 nm and eluents having retention times of 15.95 min and 17.43 min were fractionated respectively. These two eluents were concentrated under reduced pressure to give Compound 3 (yield:50.1 mg) and Compound 4 (yield:16.1 mg) as colorless waxy materials.

EXAMPLE 3

The No. 6 fraction obtained in Example 1 (a fraction eluted with a hexane solution containing 20% of ethyl acetate) was applied to reversed phase column chromatography (ODS-7515-12A, obtained from SSC) and eluted with water/methanol gradually changed from whose water concentration is 70%, 50%, 40%, 30%, to 10% to give fraction Nos. 1 to 5. The fraction No.5 (a fraction eluted with a methanol solution containing 10% of water) was purified by normal phase HPLC. A reverse phase column (Shenshu-PEGASIL, obtained from ODS, 250×10 mm) was used and acetonitrile:water=10:1 (v/v) was used as a mobile phase. The fraction was eluted at a flow rate of 4 ml/min (room temperature) and eluents were monitored by a RI detector (shodex RI-101) and eluents having retention times of 31.1 min and 37.2 min were fractionated respectively. These two eluents were concentrated under reduced pressure to give Compound 1 (yield:12.1 mg) and Compound 2 (yield:10.1 mg) as colorless waxy materials.

The fraction No. 4 (a fraction eluted with a methanol solution containing 30% of water) was purified by a normal phase HPLC. Silica gel (Shenshu-PEGASIL SILICA-60-5, 250×10 mm) was used as a stationary phase and chloroform:hexane:ethyl acetate=30:10:10 (v/v/v) was used as a mobile phase. The fraction was eluted at a flow rate of 4 ml/min (room temperature) and eluents were monitored by a UV detector at 254 nm and eluents having retention times of 8.5 min and 9.18 min were fractionated respectively. These two eluents were concentrated under reduced pressure to give Compound 3 (yield:14.0 mg) and Compound 4 (yield:1.3 mg) as colorless waxy materials.

EXAMPLE 4

The fraction No. 7 obtained in Example 1 (a fraction eluted with a hexane solution containing 30% of ethyl acetate) was applied to reversed phase column chromatography (ODS-7515-12A, obtained from SSC) and eluted with water/methanol gradually changed from whose water concentration is 70%, 50%, 40%, 30%, to 10% to give fraction Nos. 1 to 5.

A solvent of the fraction No. 2 (a fraction eluted with a methanol solution containing 50% of water) was evaporated to give a crystal. Recrystalization of the crystal from methanol gives Compound 5 (yield:200 mg) as a white needle crystal.

The fraction No. 1 (a fraction eluted with a methanol solution containing 70% of water) was purified by reversed phase HPLC. FluoFix (type:IEW205) was used as a stationary phase and 45% acetonitrile solution (acetonitrile:water=45:55 (v/v)) was used as a mobile phase. The fraction was eluted at a flow rate of 6.0 ml/min (room temperature) and eluents were monitored by a UV detector at 210 nm and eluents having retention times of 11.0 min and 12.67 min were fractionated respectively. These two fractions were evaporated and recrystalized from methanol to give Compound 6 (yield:20.0 mg) and Compound 7 (yield:10.0 mg) as a white powder and a white needle crystal respectively.

The fraction No. 3 (a fraction eluted with a methanol solution containing 40% of water) was purified by HPLC. PEGASIL ODS-2 (obtained from SSC, 250×10 mm) was used and 60% acetonitrile solution (acetonitrile:water=60:40 (v/v)) was used as a mobile phase. The fraction was eluted at a flow rate of 3.0 ml/min (room temperature) and eluents were monitored by a UV detector at 210 nm and an eluent having retention time of 26.05 min was fractionated. The fraction was evaporated and recrystalized from methanol to give Compound 8 (yield:40.1 mg) as a white needle crystal.

The MS, UV and IR data for Compounds 1 to 8 in Table 1, $^1$H NMR data for Compounds 1 to 4 in Table 2, $^{13}$C NMR data for Compounds 1 to 4 in Table 3, $^1$H NMR data and $^{13}$C NMR data for compounds 5 to 7 in Table 4, $^1$H NMR data and $^{13}$C NMR data for Compound 8 in Table 5.

TABLE 1

MS, UV, IR data for Compounds 1 to 8

| Compound | 1 | 2 | 3 | 4 |
|---|---|---|---|---|
| form | colorless oil | colorless oil | colorless oil | colorless oil |
| HR-MS (m/z) | FAB− | EI | EI | FAB+ |
| found | 685.43168 | 628.43401 | 482.30318 | 505.29259(M + Na) |
| calculated | 685.43152 | 628.43390 | 482.30320 | 505.29300($C_{30}H_{42}O_5$ + Na) |
| molecular weight | 686 | 628 | 482 | 628 |
| molecular formula | $C_{40}H_{62}O_9$ | $C_{38}H_{60}O_7$ | $C_{30}H_{42}O_5$ | $C_{30}H_{42}O_5$ |
| UV $\lambda_{max}^{MeOH}$ nm (lg ε) | 206 (2.88) | 206 (2.88) | 206 (4.11) 220 (3.94) | 205 (4.01) 220 (3.87) |
| IR $\nu^{cm-1}_{max}$ | 3440 (OH) 1742, 1725, 1718 (C=O) | 3460 (OH) 1741, 1728, 1716 (C=O) | 3456 (OH) 1720 (C=O) | 3443 (OH) 1719 (C=O) |

| Compound | 5 | 6 | 7 | 8 |
|---|---|---|---|---|
| form | white needle crystal | white powder | white needle crystal | white needle crystal |
| HR-EI-MS(m/z) | | | | |
| found | 730.28401 | 722.25664 | 722.25154 | 793.29422 |
| calculated | 730.28361 | 722.25735 | 722.25735 | 793.29454 |
| molecular weight | 730 | 722 | 722 | 793 |
| molecular formula | $C_{37}H_{46}O_{15}$ | $C_{38}H_{43}O_{14}$ | $C_{38}H_{43}O_{14}$ | $C_{41}H_{47}NO_{15}$ |
| UV $\lambda_{max}^{nm}$(lg ε) | 230 (4.00) | 231(4.23) | 230(4.21) | 225(4.10) |
| IR $\nu^{cm-1}_{max}$ | 3545 (OH) 1738 (C=O) 1648 (C=C) | 3504 (OH) 1712 (C=O) 1650 (C=C) | 3509 (OH) 1741 (C=O) 1711 (C=O) 1651 (C=C) | 3452 (OH) 1739 (C=O) 1652 (C=C) |

TABLE 2

$^1$H NMR data for Compounds 1, 2, 3, and 4 (300 MHz, CDCl$_3$, TMS, δ(ppm) (J = Hz)

| Attribution | 1 | 2 | 3 | 4 |
|---|---|---|---|---|
| H-1 | 6.01 d (1.5) | 6.03 d (1.8) | 6.07 d (1.5) | 6.07 d (1.5) |
| H-3 | 5.44 s | 5.35 s | 5.53 s | 5.48 s |
| H-5 | 3.88 d (6.9) | 3.69 s | 3.68 d (6.9) | 3.68 brs |
| H-7 | 6.07 d (3.9) | 5.71 m | 5.77 m | 5.76 m |
| H-8 | 4.06 dd (12.6, 4.5) | 3.98 m | 4.01 dd (11.7, 3.6) | 4.01 dd (11.7, 3.6) |
| H-11 | 2.56 m | 2.54 m | 2.46 m | 2.44 m |
| H$_2$-12 | 2.72 dd (16.8, 3.3) 2.19 m$^b$ | 2.70 dd (16.8, 3.3) 2.20 m$^b$ | 2.26 m$^b$ 1.75 m$^b$ | 2.26 ddd (15.9, 9.0, 3.3) 1.75 m$^b$ |
| H-13 | | | 0.67 m | 0.67 m |
| H-14 | 1.23 m$^b$ | 1.23 m$^b$ | 0.90 m$^b$ | 0.90 m$^b$ |
| Me-16 | 1.07 s | 1.05 s | 1.05 s | 1.05 s |
| Me-17 | 1.19 s | 1.18 s | 1.08 s | 1.08 s |
| Me-18 | 0.97 d (7.5) | 0.97 d (6.6) | 0.98 d (6.9) | 0.98 d (6.9) |
| Me-19 | 1.78 d (1.5) | 1.773 d (1.5) | 1.79 m$^b$ | 1.79 m$^b$ |
| H-20 | 4.73, 4.47 Abq (12.6) | 1.777 s 3H | 1.79 m$^b$ | 1.79 m$^b$ |
| 3-R$_1$ | 2.31 m 1H 1.92 m 1H 0.92 d (6.9) 3H 0.96 d (6.6) 3H 1.14 d (7.2) 3H | 2.31 m 1H 1.92 m 1H 0.92 d (6.9) 3H 0.96 d (6.6) 3H 1.14 d (7.2) 3H | 2' 5.94 d (15.3) 3' 7.68 dd (15.3, 11.7) 4' 6.16 dd (11.7, 10.5) 5' 6.14 m$^b$ 6' 2.33 m 7' 1.43 m 8', 9' 1.29 m 10' 0.89 t (7.0) | 2' 5.85 d (15.3) 3' 7.33 m 4' 6.19 m$^b$ 5' 6.19 m$^b$ 6' 2.15 m 7' 1.44 m 8', 9' 1.29 m 10' 0.89 t (7.0) |
| 13-R$_3$ | 2.19 t (7.5) 2H 1.55 m 2H 1.25 s —(CH$_2$)$_8$— 0.88 t (6.9) 3H | 2.19 t (7.5) 2H 1.55 m 2H 1.25 s —(CH$_2$)$_8$— 0.88 t (6.9) 3H | | |
| 20-R$_2$ | 20-COCH$_3$ 2.05 s 3H | | | |

TABLE 3

$^{13}$C NMR data for Compounds 1, 2, 3 and 4 (75 MHz, CDCl$_3$, TMS)

| C | 1 | 2 | 3 | 4 |
|---|---|---|---|---|
| 1 | 131.1 | 131.6 | 132.8 | 132.8 |
| 2 | 135.8$^b$ | 135.3 | 135.8 | 135.8 |
| 3 | 82.4 | 82.8 | 83.4 | 83.4 |
| 4 | 84.3 | 84.4 | 85.2 | 85.2 |
| 5 | 74.6 | 76.2 | 77.6 | 77.6 |
| 6 | 135.9$^b$ | 137.2 | 137.6 | 137.6 |
| 7 | 127.9 | 122.7 | 124.3 | 124.3 |
| 8 | 42.6 | 42.5 | 43.6 | 43.6 |
| 9 | 204.6 | 205.1 | 207.1 | 207.1 |
| 10 | 71.7 | 71.6 | 72.2 | 72.3 |
| 11 | 37.5 | 37.8 | 39.1 | 39.1 |
| 12 | 35.0 | 34.9 | 31.4 | 31.4 |
| 13 | 68.8 | 68.8 | 23.3 | 23.3 |
| 14 | 28.2 | 28.4 | 23.5 | 23.5 |
| 15 | 30.2 | 30.3 | 24.2 | 24.2 |
| 16 | 22.4 | 22.4 | 28.7 | 28.8 |
| 17 | 16.6 | 16.7 | 15.7 | 15.7 |
| 18 | 18.2 | 18.0 | 17.4 | 17.4 |
| 19 | 15.5 | 15.5 | 15.8 | 15.8 |
| 20 | 66.3 | 21.9 | 22.2 | 22.2 |
| 3-R$^1$ | | | | |
| 1' | 176.7 | 176.9 | 168.0 | 168.1 |
| 2' | 46.3 | 46.3 | 120.1 | 118.2 |
| 3' | 31.0 | 31.0 | 141.5 | 146.6 |
| 4' | 20.6 | 20.6 | 126.4 | 128.4 |
| 5' | 19.1 | 19.1 | 145.4 | 147.1 |
| 6' | 14.06 | 14.06 | 31.6 | 33.2 |
| 7' | | | 28.5 | 28.5 |
| 8' | | | 29.2 | 31.6 |
| 9' | | | 22.5 | 22.6 |
| 10' | | | 14.2 | 14.2 |
| 20-R$^2$ | | | | |
| 1'' | 170.4 | | | |
| 2'' | 21.0 | | | |
| 13-R$^3$ | | | | |
| 1''' | 173.4 | 173.5 | | |
| 2''' | 34.3 | 34.3 | | |
| 3''' | 24.7 | 24.7 | | |
| 4''' | 29.48 | 29.48 | | |
| 5''' | 29.48 | 29.48 | | |
| 6''' | 29.34 | 29.34 | | |
| 7''' | 29.22 | 29.22 | | |
| 8''' | 29.15 | 29.15 | | |
| 9''' | 29.10 | 29.11 | | |
| 10''' | 31.79 | 31.79 | | |
| 11''' | 22.60 | 22.60 | | |
| 12''' | 13.98 | 13.97 | | |

$^b$Assignments may be interchanged.

TABLE 4

$^1$H, $^{13}$C NMR data for Compounds 5–7 [(500 MHz and 125 MHz, CDCl$_3$, TMS, δ (ppm) (J = Hz))

| position | 7 $^1$H | 7 $^{13}$C | 6 $^1$H | 6 $^{13}$C | 5 $^1$H | 5 $^{13}$C |
|---|---|---|---|---|---|---|
| 1 | 4.93 s | 83.4 | 4.32 d (3.9) | 87.1 | 2.65 dd (6.4, 13.9) | 40.3 |
|   |        |      |              |      | 2.20 m |   |
| 2 |        | 80.0 |              | 78.3 | 2.12 m | 38.8 |
| 3 | 5.38 d (4.9) | 79.7 | 5.54 d (4.9) | 76.7 | 5.58 m | 74.4 |
| 4 | 3.48 m | 46.4 | 3.61 dd (11.3, 4.8) | 45.1 | 2.97 brs | 51.4 |
| 5 | 5.95 s | 74.3 | 5.91 m | 73.8 | 6.13 s | 70.1 |
| 6 |        | 135.8 |       | 135.8 |       | 145.4 |
| 7 | 5.87 s | 65.1 | 5.89 m | 64.6 | 6.39 s | 69.1 |
| 8 | 4.70 d (9.4) | 72.5 | 4.65 d (9.2) | 72.7 | 6.05 s | 71.0 |
| 9 |        | 209.3 |       | 209.5 | 5.07 s | 82.4 |
| 10 |       | 47.9 |        | 48.1 |        | 41.5 |
| 11 | 3.65 d (2.1) | 61.2 | 3.69 d (2.2) | 60.8 | 4.13 s | 77.5 |
| 12 | 3.43 m | 58.0 | 3.33 dd (2.4, 9.4) | 59.0 |        | 214.0 |
| 13 | 3.26 m | 41.6 | 3.93 m | 42.6 | 2.28 q (6.5) | 50.7 |
| 14 |        | 211.4 |       | 204.9 |        | 106.3 |
| 15 |        | 84.8 |        | 96.1 |        | 90.6 |
| 16 | 1.32 s | 19.4 | 1.31 s | 20.2 | 0.92 d (6.3) | 13.3 |
| 17 | 6.31 s | 127.9 | 6.52 brs | 128.3 | 5.24 s | 106.3 |
|    | 5.91 s |       | 5.94 brs |      | 5.14 s |       |
| 18 | 1.33 s | 21.6 | 1.34 s | 21.6 | 1.29 s | 18.6 |
| 19 | 0.85 s | 18.9 | 0.85 s | 19.0 | 1.14 s | 22.1 |
| 20 | 1.66 d (6.4) | 19.2 | 1.52 d (6.4) | 17.0 | 1.30 d (6.5) | 9.21 |
| Acetyls |   |   | Acetyls |   | Acetyls |   |
| CO-1 |   | 170.6 | CO-15 |   | 172.4 CO-3, 15 |   | 169.5 |
|      |   |       |       |   |                |   | 170.2 |
| COMe-1 | 2.13 s | 20.3 | COMe-15 2.31 s |   | 21.3 COMe-3, 15 | 1.98 s | 22.0 |
|        |        |      |                |   |                 | 2.09 s | 21.3 |
| CO-3 |   | 169.8 | CO-3 |   | 168.8 CO-5 |   | 168.8 |
| COMe-3 | 1.95 s | 20.6 | COMe-3 1.89 s |   | 20.4 COMe-5 | 1.91 s | 20.9 |
|        |        |      |                |   | CO-7 |        | 170.3 |
|        |        |      |                |   | COMe-7 | 2.18 s | 21.1 |
|        |        |      |                |   | CO-9 |        | 169.2 |
|        |        |      |                |   | COMe-9 | 2.07 s | 20.4 |
| Benzoyls |   |   | Benzoyls |   | Benzoyls |   |   |
| CO-5 |   | 164.8 |        |   | 164.9 CO-8 |   | 165.4 |
| COPh-5 1 |   | 128.3 |        |   | 128.3 COPh-8 1 |   | 130.1 |
| 2, 6 | 7.48 m | 129.1 | 7.55 m | 129.3 | 2, 6 8.03 m | 129.9 |
| 3, 5 | 6.88 m | 127.7 | 7.02 m | 127.7 | 3, 5 7.42 m | 128.3 |
| 4 | 7.09 m | 132.6 | 7.22 m | 132.8 | 4 7.53 m | 132.9 |
| CO-7 |   | 166.2 |       |   | 166.0 |   |   |
| COPh-7 1 |   | 128.6 |     |   | 128.4 |   |   |
| 2, 6 | 7.53 m | 129.4 | 7.50 m | 129.5 |   |   |
| 3, 5 | 7.02 m | 127.9 | 6.92 m | 127.8 |   |   |
| 4 | 7.24 m | 132.9 | 7.11 m | 132.8 |   |   |
| OH-2 | 2.32 s |   | OH-2 | 2.52 s |   |   |
| OH-8 | 3.53 d (9.4) |   | OH-8 | 3.54 d (9.4) |   |   |
| OH-15 | 4.11 s |   | OH-1 | 3.92 d (3.9) |   |   |

TABLE 5

NMR Spectral Data of 8 (300 MHz and 75 MHz)

| atom | 8 $^1$H | 8 $^{13}$C |
|---|---|---|
| 1 α | 2.68 dd (4.5, 12.0) | 39.9 |
| 1 β | 2.19 m$^b$ |   |
| 2 | 2.20 m$^b$ | 38.7 |
| 3 | 5.58 brs | 74.1 |
| 4 | 3.05 d (2.7) | 51.4 |
| 5 | 6.19 s | 69.5 |
| 6 |   | 144.7 |
| 7 | 6.43 s | 69.1 |
| 8 | 6.17 s | 71.0 |
| 9 | 5.36 s | 83.3 |
| 10 |   | 41.7 |
| 11 | 4.30 s | 77.4 |
| 12 |   | 213.6 |
| 13 | 2.33 q (6.6) | 50.9 |
| 14 |   | 106.4 |
| 15 |   | 90.5 |
| 16 | 0.92 d (6.0) | 13.2 |
| 17a | 5.17 s | 109.9 |
| 17b | 4.99 s |   |
| 18 | 1.21 s | 22.1 |
| 19 | 1.40 s | 18.7 |
| 20 | 1.32 d (6.5) | 9.18 |

TABLE 5-continued

NMR Spectral Data of 8 (300 MHz and 75 MHz)

| atom | 8 | |
|---|---|---|
| | $^1H$ | $^{13}C$ |
| 3-COMe | 2.09 s | 169.5 |
| | | 21.2 |
| 5-COMe | 1.95 s | 168.3 |
| | | 20.8 |
| 7-COMe | 1.51 s | 170.0 |
| | | 20.3 |
| 15-COMe | 2.00 s | 168.8 |
| | | 21.9 |
| 8-benzoyl | | 164.9 |
| | | 129.7 |
| | 8.03 m | 129.5 |
| | 7.41 m | 127.8 |
| | 7.55 m | 133.1 |
| 9-nicotinoyl | 9.18 s | 162.7 |
| | 8.77 d (4.2) | 152.7 |
| | 8.31 d (7.8) | 150.0 |
| | 7.39 m$^b$ | 137.4 |
| | | 125.0 |
| | | 123.2 |

Accordingly, the structures of Compounds 1 to 8 were identified from the dataentified from the data above as follows.

Compoud 1

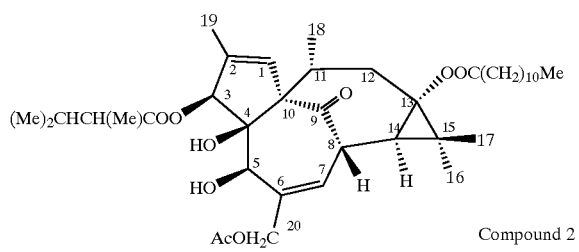

Compound 2

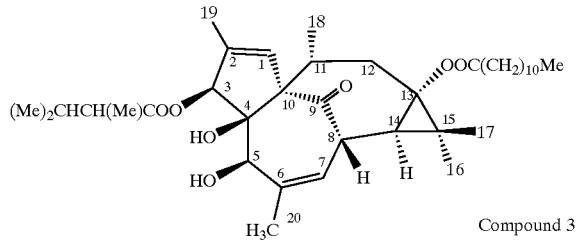

Compound 3

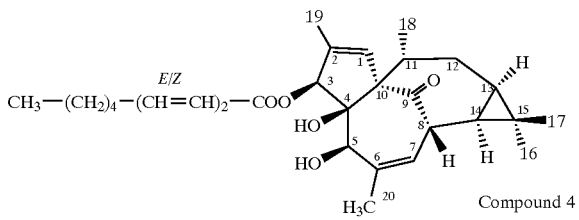

Compound 4

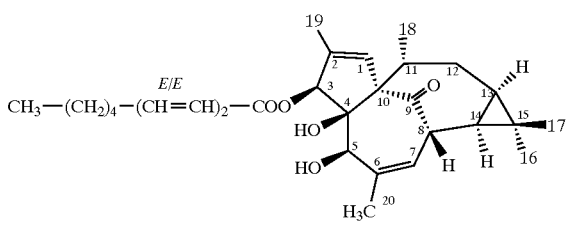

Compound 5

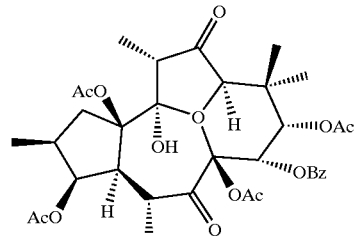

wherein, Ac represent an acetyl radical and Bz represent a benzoyl radical.

Compound 6

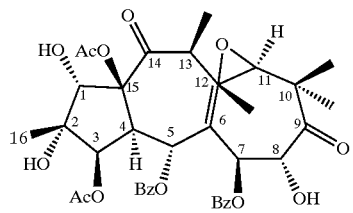

wherein, Ac represent an acetyl radical and Bz represent a benzoyl radical.

Compound 7

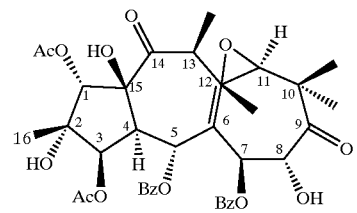

wherein, Ac represents an acetyl radical and Bz represents a benzoyl radical.

Compound 8

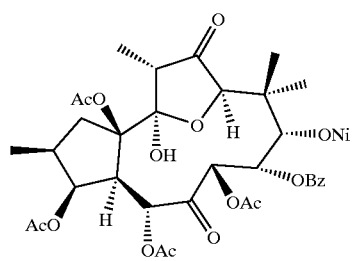

wherein, Ac represents an acetyl radical, Bz represents a benzoyl radical and Ni represents a nicotinoyl radical.

The compounds of the present invention have an inhibitory activity of cell growth as determined by an animal cap assay described in detail by S. F. Godsave and J. M. W. Slack, in Dev. Biol. 1989, 134:486–490.

Animal cap cells were dissected from Xenopus laevis at the later blastular stage. Single cells were separated from the animal cap cells and transferred to medium to prepare a cell dispersion solution.

The cell dispersion solution was added to a well of a Terasaki plate filled with a 50% animal medium containing 0.2 mg/ml of gamma-globulin. A solution containing 10 microgram/ml of the compound according to the present invention is added to the well and cultured. Next day, cell division was observed under a microscope. The inhibitory action of the compound tested is expressed a ratio of the number of non-divided cells to the total number of the cells. The results are shown in Table 6.

TABLE 6

Inhibitory activity of cell division

| Compound No. | Inhibitory ratio (%) |
| --- | --- |
| Compound 3 | 53.0% |
| Compound 4 | 55.1% |

The concentration of a compound is 10 microgram/ml.

Table 6 shows apparently that the compounds of the present invention have an inhibitory activity to cell division, and therefore, they can be useful as a therapeutic agent for treating malignant tumor, such as esophagus cancer, breast cancer, etc.

The active compounds of the present invention may be administered orally, parenterally or subcutaneously. Generally doses may be preferably from 0.1 mg/day/kg to 100 mg/day/kg for adult.

The compounds of the present invention may be administered in various forms, such as tablets, powders, granules, capsules, injections, suppositories, ointments, and cataplasms. The pharmaceutical composition containing the active compounds of the present invention may be formulated by using conventional carriers and additives such as vehicles such as resolvents, bases, diluents, fillers, adjuvants such as solution adjuvants, emulsifying agents, dispersers, disintegrants, solubilizers, viscosity-increasing agents, and lubricants, and additives such as antioxidants, preservatives, flavoring agents and sweetening agents.

The compounds of the present invention are novel diterpene compounds with antineoplastic activities, and therefore, useful as antineoplastic agents.

What is claimed is:

1. A diterpene compound represented by the formula (I):

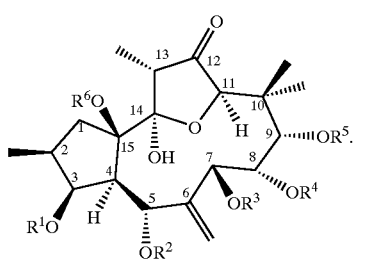

(I)

wherein $R^1$, $R^2$, $R^3$, $R^4$, and $R^6$ may be same or different and represent hydrogen atoms, linear or branched, saturated or unsaturated, substituted or unsubstituted aliphatic groups, or radicals represented by RCO-, wherein R denotes a linear or branched, saturated or unsaturated, substituted or unsubstituted aliphatic group, a substituted or unsubstituted aromatic or heteroaromatic group; and $R^5$ radicals represented by RCO-, wherein R denotes a substituted or unsubstituted heteroaromatic group.

2. A compound according to claim 1, wherein said compound is represented by the formula (III):

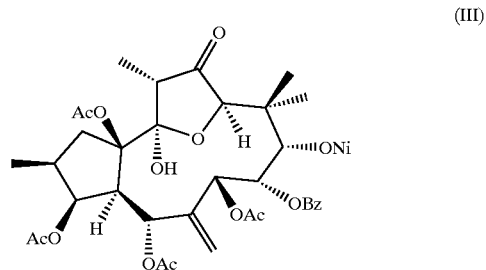

(III)

wherein Ac represents acetyl radical, Bz represents a benzoyl radical and Ni represents a nicotinoyl radical.

3. A compound according to claim 1, wherein said compound is represented by the formula (IV):

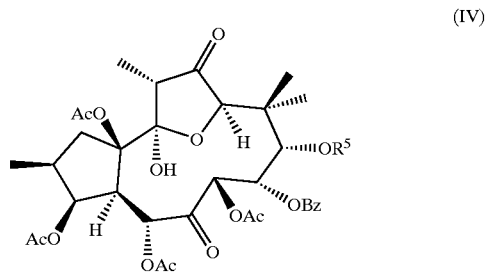

(IV)

wherein $R^5$ denotes a radical represented by the general formula RCO-, wherein R denotes a linear or branched, saturated or unsaturated, substituted or unsubstituted aliphatic group, a substituted or unsubstituted aromatic or heteroaromatic group, Ac denotes an acetyl radical, Bz denotes a benzoyl radical and Ni denotes a nicotinoyl radical.

* * * * *